United States Patent [19]

Cottenden

[11] Patent Number: 4,898,594
[45] Date of Patent: Feb. 6, 1990

[54] INCONTINENCE APPAREL FOR FEMALES

[75] Inventor: Alan M. Cottenden, Brickhill, Bedfordshire, England

[73] Assignee: National Research Development Corporation, London, England

[21] Appl. No.: 231,649

[22] Filed: Aug. 11, 1988

Related U.S. Application Data

[63] Continuation of Ser. No. 937,027, filed as PCT GB86/00120 on Mar. 6, 1986, published as WO86/05386 on Sep. 25, 1986, abandoned.

[30] Foreign Application Priority Data

Mar. 15, 1985 [GB] United Kingdom ............... 8506790

[51] Int. Cl.$^4$ ............................................ A61F 13/16
[52] U.S. Cl. .................................................. 604/397
[58] Field of Search ............ 604/358, 378, 381, 385.1, 604/385.2, 393–398, 402

[56] References Cited

U.S. PATENT DOCUMENTS

| Re. 30,972 | 6/1982 | Kyle et al. | 604/383 |
|---|---|---|---|
| 2,545,761 | 3/1951 | Brink | 604/394 |
| 2,577,398 | 12/1951 | Blake | 604/394 |
| 2,664,895 | 1/1954 | Shulman | 604/394 |
| 3,088,462 | 5/1963 | Muto | 604/394 |
| 3,459,186 | 10/1969 | Schwartz . | |
| 3,489,149 | 1/1970 | Larson | 604/394 |
| 3,532,097 | 10/1970 | Jones, Sr. | 604/366 |
| 3,719,189 | 3/1973 | Sherman | 604/381 |
| 3,838,693 | 10/1974 | Sherman . | |
| 4,229,835 | 10/1980 | Shaw | 604/385.2 |
| 4,352,356 | 10/1982 | Tong | 604/393 |
| 4,397,646 | 8/1983 | Daniels et al. | 604/381 |

FOREIGN PATENT DOCUMENTS

| 1610523 | 7/1971 | Fed. Rep. of Germany . | |
| 6611972 | 11/1967 | Netherlands | 604/393 |
| 0878455 | 9/1961 | United Kingdom | 604/396 |
| 2124072 | 2/1984 | United Kingdom . | |

Primary Examiner—C. Fred Rosenbaum
Assistant Examiner—Sharon Rose
Attorney, Agent, or Firm—Cushman, Darby & Cushman

[57] ABSTRACT

An incontinence device which includes a garment having a sewn-in absorbent pad. A sheet of liquid impervious material is interposed between the garment and the surface of the absorbent pad remote from the wearer. The absorbent pad is coupled to the sheet of liquid-impervious material by stitching then the sheet is coupled to the garment by portions of the sheet turned back from the stitching of the pad to the sheet and stitched to the garment. In a further embodiment, a layer of permeable hydrophobic material is provided intermediate the pad and the wearer.

9 Claims, 2 Drawing Sheets

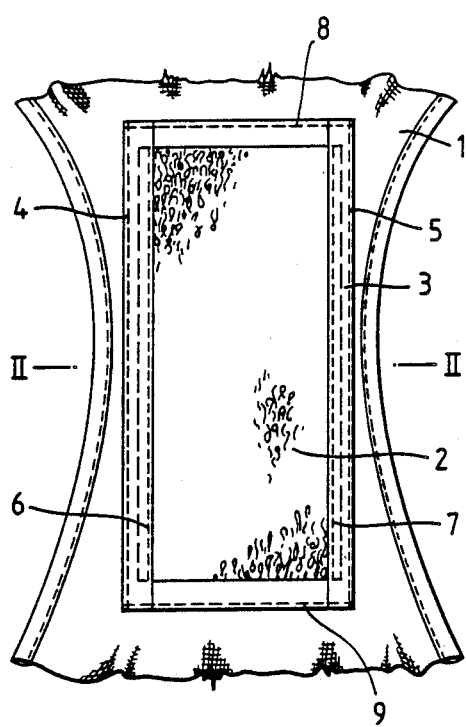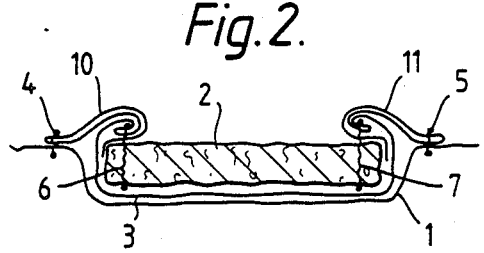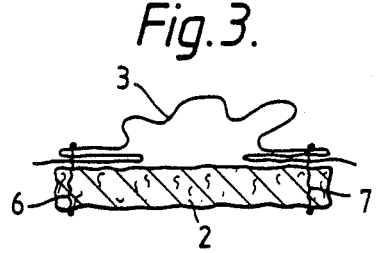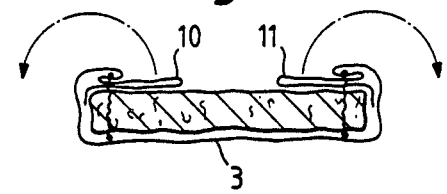

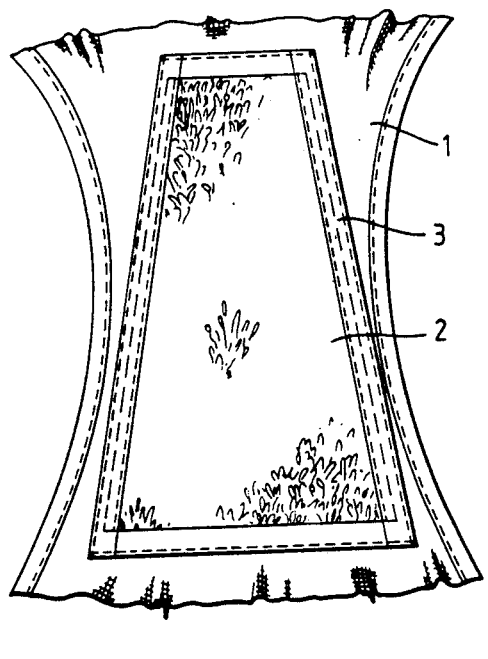
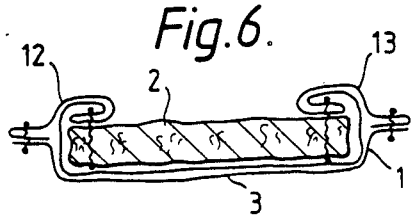
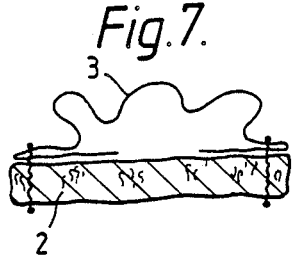
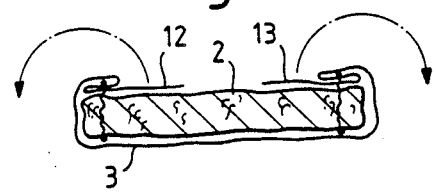
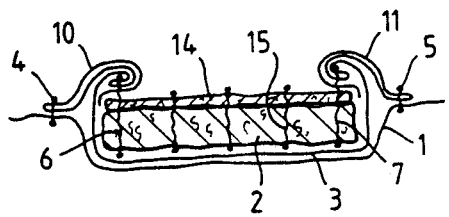
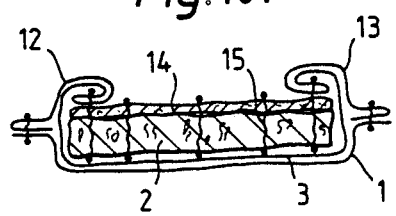

INCONTINENCE APPAREL FOR FEMALES

This is a continuation of application Ser. No. 937,027, filed as PCT GB86/00120 on Mar. 6, 1986, published as WO86/05386 on Sep. 25, 1986, now abandoned.

This invention relates to incontinence devices, and is intended to provide a garment which is washable, effective against certain forms of incontinence, comfortable to wear and lacking any stigma which, to some wearers, is sometimes attached to special garments.

It is known that many men suffer types of incontinence which manifest as an intermittent dribble of low flow rate and volume. Absorbent cone-shaped pads are commercially available for incontinent men and are secured around the penis by close fitting or stretch-net pants. However, such pouches can be difficult to retain in position, especially for the many elderly men who have a retracted penis.

Similarly, it is known that a large proportion or incontinent women suffer a leak only occasionally and, even then, in small quantities, and most of the conventional pads which many of the patients feel obliged to wear continuously are thrown away dry.

Another problem experienced with absorbent pads sewn into pants or inserted into pockets is that when the pads become wet, urine flows out by capillary action, either by contact between the wet, absorbent material and the material of the pocket or through the threads used to stitch the pocket or pad to the pants, and spreads onto and soils other garments being worn.

On purpose of the present invention is to prevent such capillary flow of urine by isolating the pants from the absorbent material of a pad sewn into the pants, which can nevertheless be laundered and re-used in the same way as a normal garment.

This invention accordingly consists of a garment for an incontinent patient including a sewn-in absorbent pad; a sheet of a liquid-impervious material interposed between the garment and the outer surface of the pad (ie the surface facing away from the patient); first stitching by which the pad is retained in position on the sheet of liquid-impervious material; and second stitching by which the sheet is fixed to the material of the garment, whereby the interposing of the sheet of liquid impervious material prevents capillary flow of urine between the material of the pad and the first stitching to the material of the garment.

The invention also encompasses a method for the manufacture of such a garment.

By way of example, the invention will now be described, with reference to the drawings, of which FIG. 1 is a plan view of the crotch portion of a garment incorporating an absorbent pad constructed in accordance with the invention, FIG. 2 is a schematic section along the line II—II of FIG. 1, FIG. 3 is a similar section through an absorbent pad illustrating the first stange of manufacture of the garment shown in FIG. 1, FIG. 4 is a similar section illustrating an intermediate stage of manufacture, FIG. 5 is similar to FIG. 1 but shows a truncated triangular pad rather than a rectangular one, and FIGS. 6, 7 and 8, corresponding to FIGS. 2, 3 and 4, show an embodiment of the invention in which the impervious sheet is singly, rather than doubly, folded before stitching to the pad.

FIGS. 9 and 10, corresponding to FIGS. 2 and 6 respectively, shows a schematic sections incorporating an additional layer of material on the absorbent pad.

With reference to FIGS. 1 and 2, a conventional paid of pants 1, made for example of cotton, includes a rectangular pad 2 of absorbent towelling material. The towelling material is selected to provide an optimum balance between high absorbency and ease of wetting on one hand, and ease of drying following laundering on the other. Polyester stretch towelling or polyester/cotton stretch towelling, for exaple, exhibit suitable properties.

An impervious sheet 3 made, for example, from polyurethane-coated nylon fabirc extends across the entire outer surface of the pad 2; this is stitched to the pants along lines 4 and 5 of longer sides of the sheet, the stitching not being in contact with the pad 2, and stitched to the inner surface of the pad 2 along lines 6 and 7 close to the sides of the pad. The pad is therefore anchored in position in fluid isolation from the material of the pants, so that urine will not escape from a wet pad into the material of the pants by capillary action through, for example, the stitching.

It is not necessary to anchor the ends of the pad to the pants; the ends of the impervious sheet are, however, stitched to the pants along lines 8 and 9.

The arrangements just described may be manufactured by using the assembly stages illustrated in FIGS. 3 and 4.

Firstly, a sheet 3 of impervious material is placed on a pad 2 of absorbent towelling material of the required size and thickness. Both long sides of the sheet are then doubly folded along the sides of the pad, and the three overlapping layers of the sheet are stitched to the pad along lines 6 and 7.

The next stage is for the sheet and pad to be turned inside out so that the sheet 3 extends across the face of the pad opposite to the face to which it is stitched (see FIG. 4). The whole is then placed on a pair of pants in the appropriate position and the two portions 10 and 11 of the sheet rotated away from the pad, as indicated by the arrow, and stitched to the pants along the lines 4 and 5 of FIGS. 1 and 2. Finally, the ends of the sheet are stitched to the pants along the lines 8 and 9 of FIG. 1.

For men, a non-rectangular pad can be employed to advantage, a truncated triangle, such as that illustrated in FIG. 5, being one appropriate shape. The method of manufacture, however, is the same as for a rectangular pad.

In an another emboidment of the invention (FIGS. 9 and 10) a layer 14 of permeable hydrophobic material, such as, for example, polyester viscose material is secured to the absorbent pad 2 to form a layer closest to the wearers' body. In use urine passes through the layer 14 away from the wearer into the absorbent pad 2, and increases the comfort of the wearer. This layer 14 can either be stitched or quitted (as shown at 15) to the absorbent pad 2 before being cut to the required shape.

Clearly, many modifications of the above arrangement and method of construction may be made within the scope of this invention. Thus, a material pervious to vapour whilst impervious to liquid may be employed to retain urine instead of the polyurethane-coated nylon fabrics. In another variation, the sheet itself may be folded once only before stitched to the pad, so that the stitching passes through two layers of the impervious sheet 3 instead of three (see FIGS. 6, 7 and 8). It can be seen from FIG. 8 that the free edges 12 and 13 of the sheet 3 are rotated outwardly to be stitched to the pants 1.

I claim:

1. A garment for use by an incontinent subject, having inner and outer surfaces respectively for location, in use, nearer to and further from said subject, and comprising:

an absorbent pad located over an area of said garment inner surface;

a sheet of liquid impermeable material having greater transverse dimensions than said area of said garment, with a central potion of said sheet being interposed between said area of said garment and said pad and with further portions of said sheet being conformed to pass over the sides of said pad and slightly across the surface of said pad remote from said area so that said sheet has a trough-like shape around said pad, remaining peripheral portions of said sheet being turned in folds to pass back across said remote surface of said pad and into engagement with said garment beyond said area;

first stitching formed through said sheet folds and said pad to interconnect the same without penetrating said area of said garment and without penetrating the portion of said sheet which is interposed between said area and said pad; and second stitching formed through said sheet peripheral portions and said garment to interconnect the same without penetrating said area of said garment and without penetrating the portion of said sheet interposed between said area and said pad.

2. A garment according to claim 1, wherein said folds are each of singly folded form.

3. A garment according to claim 1, wherein said folds are each of multiply folded form.

4. A garment according to claim 1, wherein the pad is of elongate form and the first and second stitchings each extend adjacent the longer side edges of the pad.

5. A garment according to claim 4, wherein said pad is of a rectangular shape.

6. A garment according to claim 4, wherein said pad is of a truncated triangular shape.

7. A garment according to claim 1, wherein the pad includes a layer of permeable hydrophobic material located innermost of the pad within the garment.

8. A garment according to claim 7, wherein said layer is of polyester/viscose material.

9. A garment according claim 1, wherein the overall configuration of the garment is that of a pair of pants.

* * * * *